(12) United States Patent
Benedict et al.

(10) Patent No.: US 6,627,230 B2
(45) Date of Patent: Sep. 30, 2003

(54) METHOD OF PREPARING A BONE PRODUCT BY REMOVING CANCELLOUS BONE MATRIX

(75) Inventors: James J. Benedict, Arvada, CO (US); Frank Fisher, Evergreen, CO (US); Colin Brock, Arvada, CO (US)

(73) Assignee: Centerpulse Biologics Inc., Houston, TX (US)

( * ) Notice: Subject to any disclaimer, the term of this patent is extended or adjusted under 35 U.S.C. 154(b) by 0 days.

(21) Appl. No.: 09/747,166

(22) Filed: Dec. 22, 2000

(65) Prior Publication Data

US 2002/0081959 A1 Jun. 27, 2002

(51) Int. Cl.⁷ .................. A61F 2/28; A61K 35/32; A61N 1/18; C12N 5/08
(52) U.S. Cl. .................. 424/549; 435/372; 607/51; 623/16.11
(58) Field of Search ................ 435/174, 243, 435/252.1, 283.1, 325, 404, 395, 372; 424/549; 623/16.11; 607/51

(56) References Cited

U.S. PATENT DOCUMENTS

| 2,734,537 A | 2/1956 | Geisler .................. 146/76 |
|---|---|---|
| 2,734,540 A | 2/1956 | Geisler .................. 146/222 |
| 3,722,032 A | 3/1973 | Draper et al. .................. 17/1 |
| 4,402,112 A | 9/1983 | Gasbarro .................. 17/11 |
| 4,440,750 A | 4/1984 | Glowacki et al. .............. 424/95 |
| 4,608,199 A | 8/1986 | Caplan et al. ............... 530/414 |
| 5,290,763 A | 3/1994 | Poser et al. .................... 514/21 |
| 5,333,626 A | 8/1994 | Morse et al. ............... 128/898 |
| 5,371,191 A | 12/1994 | Poser et al. ................. 530/350 |
| 5,513,662 A | 5/1996 | Morse et al. ............... 128/898 |
| 5,556,379 A | 9/1996 | Wolfinbarger ................ 604/49 |
| 5,563,124 A | 10/1996 | Damien et al. ............... 514/21 |
| 5,797,871 A | 8/1998 | Wolfinbarger, Jr. .......... 604/49 |
| 5,820,581 A | 10/1998 | Wolfinbarger, Jr. .......... 604/49 |
| 5,846,484 A | 12/1998 | Scarborough et al. ........ 422/28 |
| 5,977,034 A | 11/1999 | Wolfinbarger, Jr. ......... 510/109 |
| 5,977,432 A | 11/1999 | Wolfinbarger, Jr. et al. ... 623/16 |
| 6,024,735 A | 2/2000 | Wolfinbarger, Jr. ......... 604/500 |

Primary Examiner—David M. Naff
Assistant Examiner—Deborah K. Ware
(74) Attorney, Agent, or Firm—Kenneth S. Barrow; Timothy L. Scott

(57) ABSTRACT

A method and apparatus for preparing a bone product are provided. The method includes contacting an interior section of a cylindrical bone portion with a high pressure fluid medium such as at least about 1000 psi to remove at least a portion of cancellous bone matrix from the bone portion. Preferably the bone contains less than about 25% by weight cancellous bone. The apparatus includes multiple stations of opposing high pressure nozzles holding the cylindrical bone portion from each end and for contacting the interior surfaces of a bone portion with a fluid medium. The apparatus also includes a third nozzle for contacting the exterior surface of the bone portion with a fluid medium.

12 Claims, 2 Drawing Sheets

METHOD OF PREPARING A BONE PRODUCT BY REMOVING CANCELLOUS BONE MATRIX

FIELD OF THE INVENTION

This invention relates to an apparatus and method for preparing a bone product. Specifically, the present invention relates to an apparatus and method for removing cancellous bone matrix, bone marrow and soft tissue from a bone portion.

BACKGROUND OF THE INVENTION

Materials derived from bone, i.e., bone derivatives, such as bone powder, demineralized bone, biologically active proteins and collagens are used in a variety of applications, for example, replacing or repairing bone; covering or filling bone defects; as an osteogenic agent; and making photographic films, medical devices and bone meal. Bone derivatives are isolated or prepared from a cleaned bone product.

Generally, a bone product is made by removing undesired materials such as cancellous bone matrix, bone marrow and/or soft tissue from a bone. For example, in bone grafting, bone marrow is removed prior to being grafted on to a recipient to reduce the incidence of immune response. In a process for using a bone product as an osteogenic agent, the preparation of a bone product can involve physically cleaning the surface of a bone to remove periosteum and other soft tissues by scraping or brushing. The bone is then crushed into small fragments and washed with water to remove any water soluble materials remaining on the fragments. The fragments are then dried and extracted with lipophilic solvents, such as ethanol and ethyl acetate, to remove lipids. The fragments are then demineralized with acid and sterilized by irradiation, chemical sterilization, or other known solid sterilization techniques. This method of bone product preparation is time consuming and requires the use of organic solvents to remove remnants of soft tissues and other lipophilic compounds.

Another method for preparing a bone product is by comminuting a bone to a desired size and removing the soft tissues, such as meat and fat, that are present on the bone by a process such as a froth flotation process. For example, bone particles containing soft tissue are placed in a water bath and the air bubbles are introduced along with other chemicals to separate and remove soft tissue from bone fragments. One of the drawbacks of this process is that it requires time-consuming effort to remove undesired material from the bone particles. Another disadvantage of this process is that comminuting the bone lyses bacteria that are present on the bone thus releasing endotoxins and possibly contaminating bone particles with endotoxins.

Another drawback to this method is the use of organic solvents to remove lipids which may require expensive waste disposal. Moreover, this method requires comminuting unnecessary bone materials, which must be removed at a later stage of bone product preparation. Hence, a large amount of waste undergoes the same processing as the desired material, which can increase the overall cost.

U.S. Pat. No. 5,333,626 issued to Morse et al. ("the '626 patent") discloses a method for preparing a bone product for a transplantation. The method involves cleaning a bone with a detergent at a high-pressure and elevated temperature to remove bone marrow while retaining the cancellous bone matrix. The '626 patent requires primary decontamination of bone in order to remove bacteria and/or fungi which may be present on the bone. The bone is then cleaned using the high-pressure detergent without removing cancellous bone matrix. The method also requires repeated washing with sterile water to remove any detergent residue that may be left behind during the cleansing process.

Therefore, there is a need for preparing a bone product which removes a substantial portion of the undesired materials prior to comminuting the bone portion. There is also a need for reducing endotoxin contamination of a bone product during a comminuting process. In addition, there is a need for a simple and fast method for removing soft tissues without using an organic solvent or a froth flotation process.

SUMMARY OF THE INVENTION

The present invention includes a method for preparing a bone product which includes contacting an interior section of a bone portion with a first fluid medium to remove at least a portion of cancellous bone matrix from the bone portion. In one aspect, the pressure of the first fluid medium is at least about 3000 psi. The first fluid medium is preferably water. The method preferably includes removal of substantially all cancellous bone from the bone portion. The method can also include contacting an exterior section of the bone portion with a second fluid medium to remove at least a portion of soft tissue from the bone portion. By practice of the method, the resulting bone product can have a minimal amount of endotoxin, preferably less than about 300 $\mu$g/g of the bone product, more preferably less than about 100 $\mu$g/g of the bone product, more preferably less than about 50 $\mu$g/g of the bone product, more preferably less than about 10 $\mu$g/g of the bone product, and even more preferably less than about 1 $\mu$g/g of the bone product.

A further embodiment of the present invention is an apparatus for preparing a bone product from a cylindrical bone portion. The apparatus includes a first interior nozzle for discharge of a pressurized fluid medium toward an interior surface of the bone portion and a retainer for retaining the bone portion so that an interior surface of the bone portion is exposed to the pressurized fluid medium. The apparatus also includes a fluid medium supply to supply fluid medium to the first interior nozzle at a pressure sufficient to remove at least a portion of cancellous bone matrix from the bone portion. In one embodiment of the apparatus, the pressurized fluid medium is discharged at a pressure of at least about 3000 psi. The apparatus can also include a second interior nozzle for discharge of a pressurized fluid medium toward an interior surface of the bone portion where the second interior nozzle is in opposing relation to the first interior nozzle. In a further embodiment, the retainer is made up of the first and second interior nozzles positioned to engage the interior circumference of first and second open ends, respectively, of the cylindrical bone portion.

The apparatus can also include a third exterior nozzle for contacting an exterior surface of the bone portion with a pressurized fluid medium. In this embodiment, the third exterior nozzle can direct the pressurized fluid medium toward the bone portion at an angle of incidence non-perpendicular to a tangent of the bone portion.

The apparatus can also include multiple sets of first, second and third nozzles arrayed in a circular configuration on a base. In this embodiment, the base can be indexed to rotate each of the sets of nozzles to a bone portion engagement station and to a bone product discharge station.

A further embodiment of the present invention is a method for producing a biologically active protein which includes removing soft tissue, marrow and cancellous bone matrix from a bone portion with a pressurized fluid medium to produce a bone product. This method further includes recovering a biologically active protein from the bone product. This method can also include demineralizing and/or comminuting the bone product before the step of recovering a biologically active protein.

A further embodiment of the present invention is a bone product comprising less than about 25% by weight cancellous bone matrix. Such a bone product can also have less than about 300 µg of endotoxin per gram of the bone product. Such a bone product can also have less than about 25% by weight marrow.

DETAILED DESCRIPTION OF THE INVENTION

Figure 1:
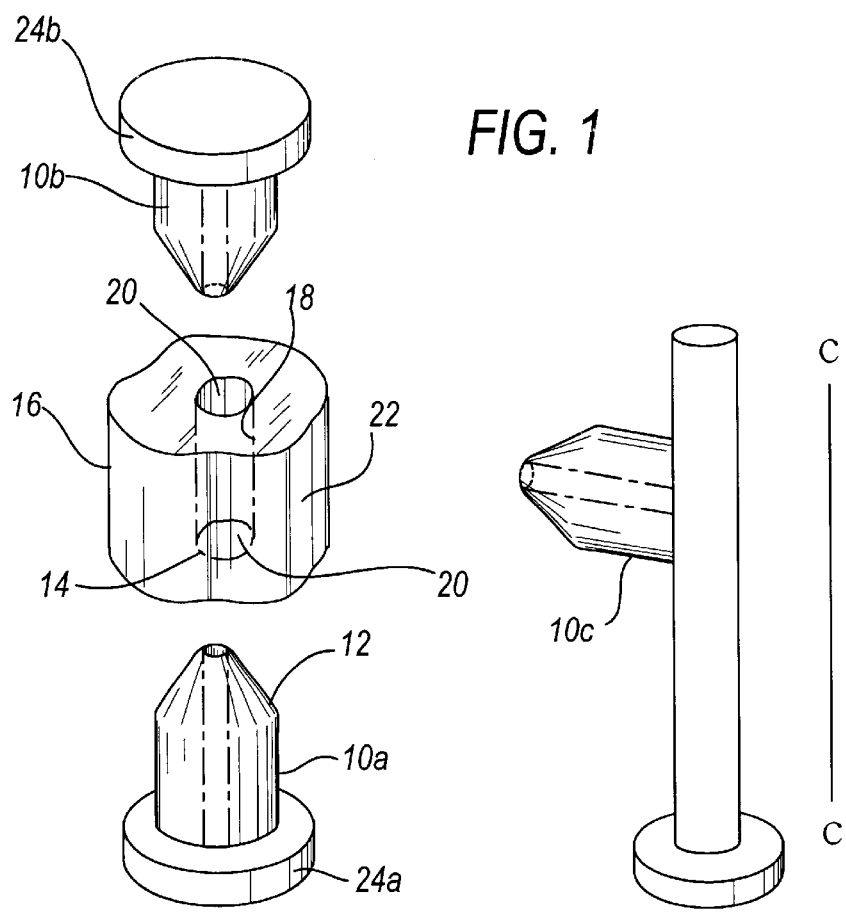
FIG. 1 shows an expanded side view of a single bone portion treating station of the apparatus of the present invention.

As used in this invention, the term "bone product" refers to a bone portion in which cancellous bone matrix, bone marrow and/or soft tissue have been at least partially removed. The term "bone portion" refers to a piece of any type of human or animal bone which has been cut or processed to expose an interior section of the bone. An interior section of a bone refers to a cross section of a bone where bone marrow and/or cancellous bone matrix is present. The present invention provides a method and apparatus for preparing a bone product from a bone portion. The length of a bone portion which is useful for preparing a bone product is from about 5 cm to about 45 cm, preferably from about 10 cm to about 40 cm, and more preferably from about 10 cm to about 20 cm. A wide variety of the average cross section diameter of the bone portion can be processed by the present invention. The cross section diameter will be determined simply by the diameter of the natural bone from which the bone portion is derived. Preferably, the average cross section diameter of the bone portion is from about 1 cm to about 15 cm, more preferably from about 3 cm to about 12 cm, and most preferably from about 5 cm to about 9 cm.

A bone portion can be prepared from any type of bone, but is preferably prepared from long bones, such as a femur. By cutting the bone transverse to the long axis of the bone, rings of bone are prepared which are highly suitable for use in the present invention. Thus, each such ring or cylindrical bone portion will have first and second open ends, and each open end has an interior circumference. The process of the present invention includes contacting an interior section of a bone portion with a first fluid medium to remove at least a portion of cancellous bone matrix from the bone portion. The term "cancellous bone" means the reticular, spongy, or lattice-like structure of the bone. The fluid medium can be a liquid or a gas with or without entrained solids. Preferably the fluid medium is a liquid. The liquid can be any liquid which can clean the bone, for example, the liquid can include a detergent, surfactant, organic solvent, water or a mixture thereof. Preferably, the liquid is water. Other components can be added to water to facilitate preparation of the bone portion. For example, a surfactant can be added to water to aid in removing fat from the bone portion. The first fluid medium is typically at a temperature of between about 2° C. to about 75° C., more preferably between about 4° C. to about 45° C., and more preferably between about 10° C. to about 40° C.

The fluid medium spray has sufficient pressure to remove at least a portion of cancellous bone matrix along with marrow, from the bone portion. Preferably, the pressure of the first fluid medium spray is sufficiently high to remove substantially all cancellous bone matrix and bone marrow. As used in this invention, removal of substantially all cancellous bone matrix refers to removal of at least about 25% by weight of cancellous bone matrix, preferably at least about 50% by weight, and more preferably at least about 75% by weight. Removal of substantially all bone marrow refers to removal of at least about 25% by weight of bone marrow, preferably at least about 50% by weight, and more preferably at least about 75% by weight. Alternatively, the bone product prepared by the process of the present invention contains less than about 25% by weight cancellous bone matrix, preferably less than about 15% by weight, and more preferably less than about 5% by weight. Alternatively, the bone product prepared by the process of the present invention contains less than about 25% by weight bone marrow, preferably less than about 15% by weight and more preferably less than about 5% by weight.

Although bone marrow can be removed with a relatively low fluid medium spray pressure, removal of cancellous bone matrix requires higher fluid medium spray pressure. Hence, the pressure of the first fluid medium spray is at least about 1000 psi, preferably at least about 2500 psi, more preferably at least about 4000 psi, and more preferably at least about 5000 psi. The interior section of the bone portion is contacted with the first fluid medium spray for a time sufficient to remove a desired amount of cancellous bone. It should be appreciated that, as expected, a low fluid medium spray pressure requires longer contact time in order to remove a desired amount of cancellous bone matrix and bone marrow. Typically, the length of contact time of an interior section of a bone portion with a fluid medium is from about 15 seconds to about 300 seconds, preferably from about 30 seconds to about 240 seconds, and more preferably from about 60 seconds to about 120 seconds.

As cancellous bone matrix is removed by the first fluid medium spray, the distance between the orifice for delivery of the first fluid medium and the interior of the bone portion increases. This increase in the distance results in less fluid medium spray pressure applied to the interior of the bone portion which can reduce the effectiveness of cancellous bone matrix removal by the fluid medium spray. This reduction in effectiveness can be prevented by having the fluid medium spray pressure to be sufficiently high to allow substantially complete removal of cancellous bone matrix along the entire length of the bone portion. Alternatively, a relatively constant fluid medium spray pressure can be applied to substantially all cancellous bone matrix by moving a nozzle for the first fluid medium spray along the length of the bone portion as the removal of cancellous bone matrix progresses. Thus, the first spray nozzle can be made to be movable along the direction substantially co-axial to the length of the bone portion.

The bone preparation process of the present invention can also include contacting an exterior section of the bone portion with a second fluid medium to remove at least a portion of soft tissue from the bone portion. An exterior section of a bone refers to the outer layer of the bone portion. The second fluid medium, and temperature thereof for treating the exterior of the bone portion, can be the same as or different from the first fluid medium used to treat the interior of the bone. Since no cancellous bone matrix is removed by the second fluid medium spray, the pressure of second fluid medium spray need not be as high as the first fluid medium spray. But rather than using two separate fluid pressurizing systems, it may be more economical to use the same fluid pressurizing system to generate both the second fluid medium spray and the first fluid medium spray. The pressure of the second fluid medium spray is at least about 1000 psi, preferably at least about 2500 psi, more preferably at least about 4000 psi, and more preferably at least about 5000 psi. Preferably, the second fluid medium spray removes substantially all soft tissue from the bone portion. Soft tissue refers to any non-bone tissue that is attached to the exterior section of a bone portion. As used in this invention, a bone product having substantially all soft tissue removed refers to a bone product having less than about 500 mg of soft tissue remaining per gram of the bone product which has been prepared using the apparatus or method of the present invention, preferably less than about 100 mg, and more preferably less than about 25 mg. Alternatively, the bone product contains less than about 25% by weight of soft tissue, preferably less than about 15% by weight, and more preferably less than about 10% by weight.

The second fluid medium spray contacts the bone portion at an angle of incidence non-perpendicular to a tangent of the bone portion. This non-perpendicular angle of incidence provides a better shearing action for removing soft tissue from a bone portion than having the second fluid medium spray contacting a tangent of the bone portion perpendicularly.

The method of bone product preparation of the present invention produces resulting bone product that contains low levels of endotoxins. Comminuting bone containing soft tissue, bone marrow, and/or cancellous bone or separating soft tissue, bone marrow, and/or cancellous bone by a froth flotation process can lyse bacteria that are present in the bone and/or the soft tissue, bone marrow, and/or cancellous bone thereby releasing endotoxins, such as pyrogen, and other harmful compounds. Moreover, a froth flotation process requires immersing the bone in a solution, which may be contaminated by endotoxins and other harmful compounds, further increasing the likelihood of contamination. The present invention removes the soft tissue, cancellous bone and bone marrow prior to any comminution of the bone product and without immersing the bone portion in a solution. Therefore, the risk of endotoxin contamination in the bone product is greatly reduced or eliminated. The bone product prepared by the present invention contains less than about 300 $\mu$g of endotoxin per gram of prepared bone product, preferably less than about 100 $\mu$g, more preferably less than about 50 $\mu$g, more preferably less than about 10 $\mu$g and even more preferably less than about 1 $\mu$g.

The first and second fluid media, after contact with the bone portion, can be collected, filtered to remove undesired materials and recycled, thus reducing the total amount of fluid medium used in the process. Such filtering can be directed to remove soft tissue, cancellous bone matrix and/or marrow. The treated fluid medium can also be sterilized with appropriate chemicals to remove undesired materials or contaminants.

The present invention also includes an apparatus for preparing a bone product from a cylindrical bone portion, which is useful in the method generally described above.

The apparatus of the invention includes nozzles for discharge of a fluid medium. The fluid medium is as generally described above and the operational parameters of the nozzles are selected so as to achieve the fluid pressures as described above. For example, with reference to FIG. 1, a bone product preparation apparatus of the present invention is illustrated. Nozzles 10a, 10b, 10c are shown. As can be seen in FIG. 1, the nozzles 10a, 10b, 10c can have a shoulder 12 which is suitable for engagement of the interior circumference 14 of an open end of a bone portion 16. In the embodiment illustrated, a first nozzle 10a and a second nozzle 10b are positioned to discharge a fluid medium to the interior surface 18 of a bone portion 16 from both ends 20 of the cylindrical bone portion 16.

The apparatus further includes a retainer for positioning an interior surface 18 of the bone portion 16 in line with a nozzle 10a, 10b. In this manner, fluid being discharged from the nozzle can contact interior surfaces 18 of the bone portion 16 to remove marrow and cancellous bone therefrom.

The apparatus of the present invention further includes a fluid supply mechanism. Such a mechanism includes a fluid source and a mechanism for generating pressure on the fluid, such as by a pressure pump such as those available from National Liquid Blasting Corp. (City, Country). The fluid supply mechanism is suitable for generating the fluid pressures as generally described above with regard to the method of the present invention.

Figure 2:
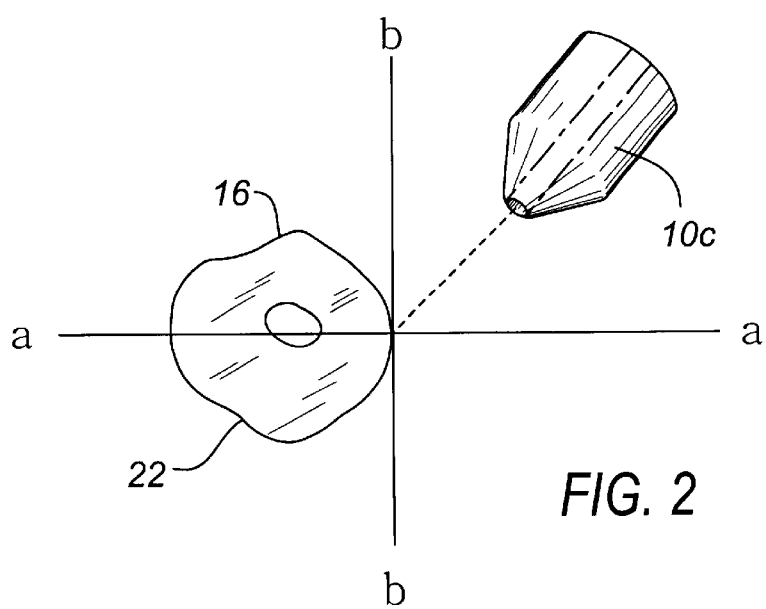
FIG. 2 shows a top view of the angle of incidence of a fluid medium from a nozzle contacting the exterior of a bone portion.

In a further embodiment of the apparatus of the present invention, the apparatus includes a third nozzle 10c for discharge of a fluid medium to the exterior surface 22 of a bone portion 16. The retainer positions the bone portion 16 such that the third nozzle 10c discharges fluid medium onto an exterior surface 22 of the bone portion 16. As is generally described above with regard to the method of the present invention and shown in FIG. 2, the third nozzle 10c directing fluid medium onto the exterior surface 22 of the bone portion 16 is positioned such that the angle of incidence of the fluid medium is not along a line perpendicular a—a to a tangent b—b of the bone portion 16.

The retainer in the apparatus of the present invention can be of a variety of designs which are conventionally known in the art. For example, the retainer can be a bracket or a clamp which retains the bone portion 16 in correct position with regard to a nozzle 10 directing fluid media. In a further embodiment, the retainer can be formed by two directly opposing nozzles 10a, 10b which are positioned such that the cylindrical bone portion 16 is held by them. In this embodiment, each nozzle 10 has a shoulder portion 12 which is large enough in diameter such that as it is brought into contact with the opening 14 of one end of the cylindrical bone portion 16, it contacts the opening. Thus, as the two opposing nozzles are brought together, they engage the cylindrical bone portion 16. Subsequently, during processing of the cylindrical bone portion 16, fluid medium is discharged from both opposing nozzles 10a, 10b to clean the interior surface 18 of the bone portion 16.

In a further embodiment of the apparatus of the present invention, the retainer for positioning the bone portion 16 with regard to a nozzle 10c directed toward an exterior surface 22 of the bone portion 16 can rotate the bone portion 16 so that the entire exterior surface 22 of the bone portion 16 is exposed to the fluid medium being discharged from the nozzle 10c. In particular, when the retainer is comprised of two opposing nozzles 10a, 10b which retain the bone portion 16 and also discharge fluid medium toward interior surfaces of the bone portion 16, the two opposing nozzles 10a, 10b, themselves, can rotate, thereby exposing the entire outer surface 22 of the bone portion 16 to a third nozzle 10c. For example, in this embodiment, the nozzles 10a, 10b can have nozzle bases 24a, 24b, about which the nozzles 10a, 10b rotate, thereby spinning the cylindrical bone portion 16 about a longitudinal axis.

In a further embodiment, a nozzle 10c positioned to discharge fluid for contact with an exterior surface 22 of a bone portion 16 reciprocates in the direction c—c of the longitudinal axis of the bone portion 16. In this manner, as the bone portion is rotated about its longitudinal axis and the nozzle reciprocates along a line parallel to the longitudinal axis of the bone portion, the entire exterior surface 22 of the bone portion is directly exposed to the nozzle 10c.

Figure 3:
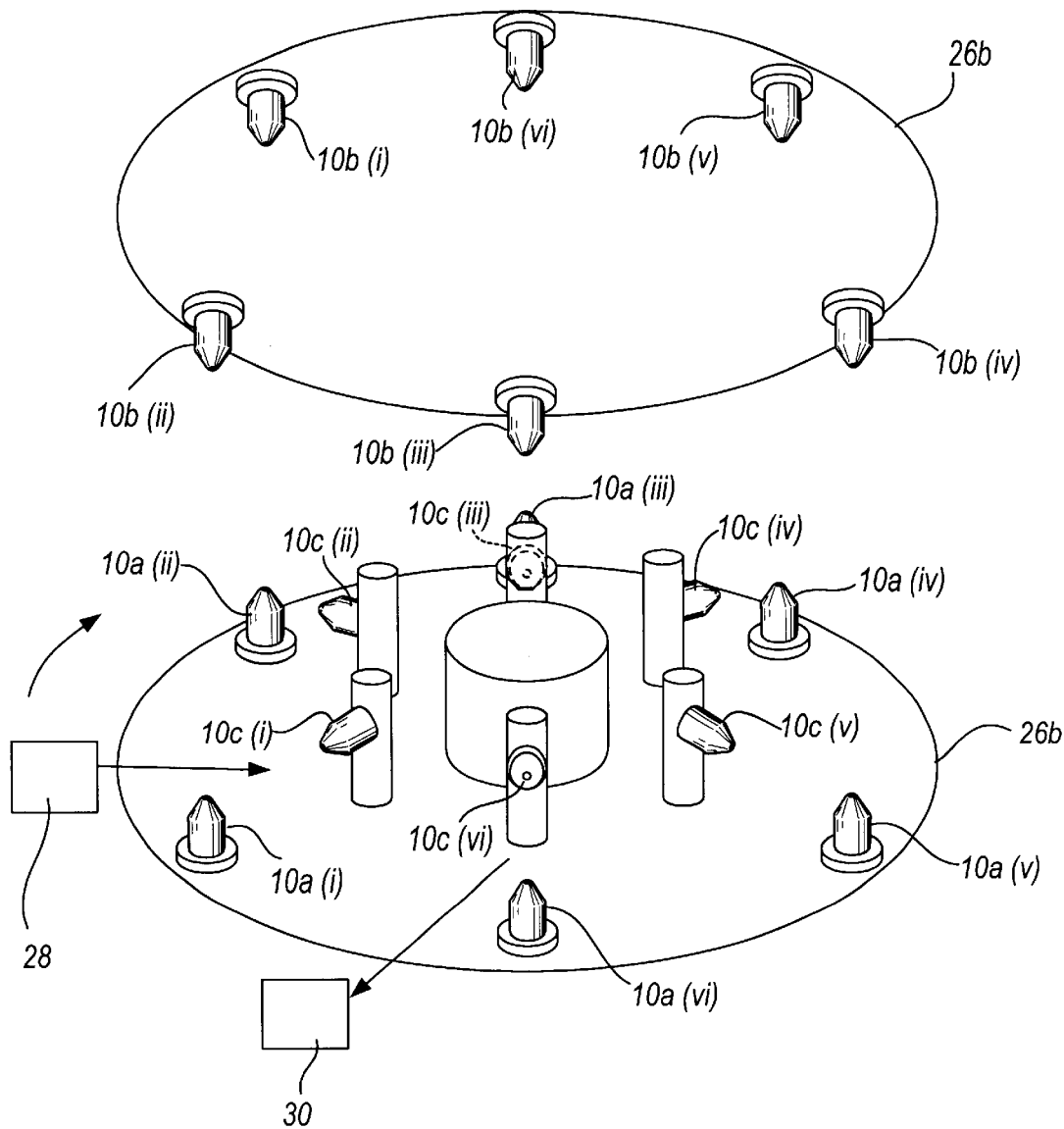
FIG. 3 is an expanded side view of an apparatus of the present invention having multiple bone portion treating stations.

The present invention is also directed toward an apparatus for preparing multiple bone products from multiple cylindrical bone portions. Such an apparatus has two or more stations at which the bone portions are processed. Each such station comprises an apparatus as generally described above comprising first and second nozzles 10a, 10b for cleaning the interior surface 18 of a bone portion 22 and a third nozzle 10c for cleaning the exterior surface 22 of a bone portion. An expanded view of such an apparatus is illustrated in FIG. 3. As can be seen in FIG. 3, this apparatus generally comprises two opposing platters 26a, 26b. The bottom platter 26a can include the first nozzles 10a(i)–10a(vi) for cleaning the interior surface 18 of multiple bone portions 16. The bottom platter 26a can also include the third nozzles 10c(i)–10c(vi). The top platter 26b can include the second nozzles 10b(i)–10b(vi) for cleaning the interior surface 18 of multiple bone portions 16.

In operation, the top and bottom platters 26a, 26b are in close enough proximity that the various pairs of first and second nozzles 10a, 10b can function to retain a bone portion as described above. As operation is initiated, a first bone portion is entered into the apparatus from a bone portion engagement station 28, for example by the first and second nozzles 10a(i), 10b(i) opening for insertion of the bone portion 16 and closing for engagement. The top and bottom platters are then rotated in a clockwise direction so that the first and second nozzles 10a(vi), 10b(vi) are indexed into alignment with the bone portion engagement station 28 and loaded with a bone portion 16 in the same manner. As the top and bottom platters are being rotated and the various stations being loaded with bone portions, cleaning operations are commenced with fluid media being discharged from nozzles in loaded stations. Also, the bone portions are rotated by the first and second nozzles 10a, 10b to allow for full processing from the third nozzle 10c. As the top and bottom platters are being indexed, the bone portion in the first station of nozzles 10a(i), 10b(i) is ultimately brought into alignment with the bone product discharge station 30 and the fully processed bone product is released from the station.

Upon subsequent indexing, the first station of nozzles 10a(i), 10b(i) is again brought into alignment with the bone portion engagement station 28.

The apparatus of the present invention can also include a cover or housing (not shown) to retain the fluid media within the apparatus. Appropriate housing devices are well known to those of skill in the art. Also, the apparatus can include fluid media collection and treatment systems (not shown). Such fluid media collection and treatment systems are well known to those of skill in the art.

The bone product produced by the bone product preparation apparatus of the present invention can be used for any purpose where a bone product is required, including isolation of biologically active proteins, bone meal preparation, photographic films, gelatins in medical devices and other useful purposes. The bone product can be comminuted to provide bone product particles of a desired size for a particular application. The comminuted bone product particles can be subjected to a size separation process to provide bone product particles of a desired size for a particular purpose.

The bone product can also be demineralized as an initial step in the production of collagen and biologically active proteins. Demineralization of bone is well known in the art and is disclosed, for example, in U.S. Pat. No. 4,440,750, issued to Glowacki et al., which is incorporated herein by reference in its entirety. The resulting collagen and protein solids can be separated from demineralization solution by any solid-liquid separation technique such as centrifugation, filtration, precipitation, and sedimentation. The solid phase contains a variety of materials including collagen and proteins. Proteins can be further recovered from the solid phase. Processes for recovery of biologically active proteins are disclosed in U.S. Pat. No. 4,608,199, issued to Caplan et al., and U.S. Pat. No. 5,290,763, issued to Poser et al. which are incorporated by reference herein in its entirety. Generally, addition of guanidine-hydrochloric acid to the solid phase solubilizes proteins, and a desired protein is then isolated by protein separation techniques well known in the art of protein separation. In this manner, biologically active proteins can be isolated which can be used in a variety of applications, including as an osteoinductive agent.

The solid phase of demineralized bone product produced by the apparatus and/or the method of the present invention contains low amount of fatty acids. Preferably, the bone product of the present invention contains less than about 1000 μg of fatty acid per gram of the prepared bone product, more preferably less than about 500 μg, and most preferably less than about 250 μg. Collagen containing a low amount of fatty acid is useful in a variety of applications including in preparation of a high speed photographic film such as x-ray films. A method for making photographic film from collagen is well known to one of ordinary skill in the art.

Another advantage of the bone product preparation apparatus of the present invention is that a bovine bone product prepared by the apparatus of the present invention reduces or eliminates the risk of possible transmission of bovine spongiform encephalitis (BSE). It is believed that the bone marrow of a bovine bone harbors the virus that causes bovine spongiform encephalitis (BSE). The bone product preparation method and apparatus of the present invention removes bone marrow from a bone portion. By removing the bone marrow and in effect cleaning the bone portion with a high pressure fluid medium spray without immersing the bone portion in a solution, the bone product preparation apparatus of the present invention reduces the amount of or completely removes the virus that causes BSE from the bone portion. Thus, the prepared bone product of the present invention can be used to isolate collagen which can be used in medical applications or devices which use gelatin. Since the bone marrow is removed prior to isolating collagen, the risk of BSE from a medical device made from collagen isolated from the bone product prepared by the apparatus of the present invention is greatly reduced or eliminated. Preparation of gelatin from collagen for medical use is well known to one of ordinary skill in the art.

The bone product prepared by the apparatus of the present invention can also be used in bone meals. Because the bone product of the present invention lacks soft tissue, a bone meal prepared by the bone product of the present invention will not spoil and create a rancid odor.

The bone product can also be used to prepare an implantable putty which is disclosed in U.S. patent application No. 09/023,617, entitled "Implantable Putty Material," filed on Feb. 13, 1998, by Benedict et al., which is incorporated herein by reference in its entirety.

The apparatus of the present invention can be used in a slaughter house for processing an animal carcass. For example, after cutting meat from a bone to produce a first meat product, the bone can be cut to form a bone portion by exposing an interior section of the bone. The bone portion can then be subjected to the process of the present invention to remove soft tissue, marrow and cancellous bone matrix to produce a second meat product and a bone product. The second meat product can then be processed to provide a variety of products such as a pet food.

Having a slaughter house process a bone portion according to the process of the present invention provides a numerous advantages. For example, a waste disposal facility which is already present in the slaughter house can be taken advantage of to reduce a separate waste disposal step that may be required in other facilities. Additionally, preparing a bone product in a slaughter house eliminates a need for freezing the bone and/or the bone portion because it does not have to be shipped to a separate processing center. This will reduce the cost of the bone product. Moreover, non-frozen soft tissue is easier to remove than frozen soft tissue; therefore, the pressure of the second fluid medium spray can be lower to remove soft tissue compared to a frozen bone portion. In addition, the transportation cost of the bone product will be lower because the prepared bone product has higher density of bone material compare to bone materials containing soft tissues.

The apparatus of the present invention can also be used in hospitals or bone banks to prepare bone products for grafting, transplanting or other medical purposes.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for preparing a bone product, comprising:

exposing an interior section of a bone portion to provide an interior bone surface; and directly contacting said interior bone surface with a first fluid medium to remove cancellous bone matrix from the bone portion, to form a resulting bone product containing less than about 25% by weight cancellous bone matrix.

2. The method of claim 1, wherein the first fluid medium has a pressure of at least about 1000 psi.

3. The method of claim 1, wherein the first fluid medium comprises a liquid.

4. The method of claim 3, wherein the liquid is water.

5. The method of claim 1, wherein the first fluid medium is a gas comprising entrained solid particles.

6. The method of claim 1, further comprising:

contacting an exterior section of the bone portion with a second fluid medium to remove at least a portion of soft tissue from the bone portion.

7. The method of claim 6, wherein substantially all soft tissue is removed from the bone portion.

8. The method of claim 6, wherein the second fluid medium has a pressure of at least about 1000 psi.

9. The method of claim 6, wherein the second fluid medium comprises a liquid.

10. The method of claim 9, wherein the liquid is water.

11. The method of claim 1, wherein the resulting bone product has an amount of endotoxin less than about 300 μg/g of the bone product.

12. The method of claim 1, wherein the first fluid medium is at a temperature of from about 4° C. to about 50° C.

* * * * *